(12) United States Patent
Ben-Asouli et al.

(10) Patent No.: US 7,264,703 B2
(45) Date of Patent: Sep. 4, 2007

(54) GEL TRAP FOR ELECTROPHORESIS

(75) Inventors: Yitzhak Ben-Asouli, Kfar Hanagid (IL); Farhat Osman, Sachnin (IL)

(73) Assignee: Gene Bio-Application Ltd., Kfar Hanagid (IL)

( * ) Notice: Subject to any disclaimer, the term of this patent is extended or adjusted under 35 U.S.C. 154(b) by 797 days.

(21) Appl. No.: 10/422,062

(22) Filed: Apr. 23, 2003

(65) Prior Publication Data

US 2004/0020776 A1 Feb. 5, 2004

Related U.S. Application Data

(63) Continuation of application No. PCT/IL01/01000, filed on Oct. 29, 2001.

(30) Foreign Application Priority Data

Nov. 2, 2000 (IL) .................................. 139446
Nov. 2, 2000 (IL) .................................. 139447

(51) Int. Cl.
*G01N 27/453* (2006.01)

(52) U.S. Cl. .................. 204/615; 204/606; 204/616

(58) Field of Classification Search ................ 204/456, 204/466, 469, 606, 616, 615
See application file for complete search history.

(56) References Cited

U.S. PATENT DOCUMENTS

| 3,803,020 | A | 4/1974 | Stephan |
| 3,873,433 | A | 3/1975 | Seidel et al. |
| 3,888,759 | A | 6/1975 | Elson et al. |
| 3,930,983 | A | 1/1976 | Sieber |
| 4,709,810 | A | * | 12/1987 | Mayes ........................ 206/205 |
| 4,830,725 | A | * | 5/1989 | Berninger et al. .......... 204/620 |
| 5,064,769 | A | | 11/1991 | Gambert et al. |
| 5,228,971 | A | | 7/1993 | Brumley, Jr. et al. |
| 5,443,704 | A | | 8/1995 | Kirkpatrick et al. |
| 5,582,702 | A | | 12/1996 | Cabilly et al. |
| 5,827,418 | A | | 10/1998 | Haven et al. |
| 5,865,974 | A | * | 2/1999 | Cabilly et al. .............. 204/456 |

FOREIGN PATENT DOCUMENTS

| DE | 32 32 685 A1 | 3/1984 |
| EP | 0199 470 A2 | 10/1986 |
| EP | 0 471 949 A1 | 2/1992 |
| EP | 0971 229 A1 | 1/2000 |
| WO | WO/92/17259 A1 | 10/1992 |
| WO | WO95/14921 | 6/1995 |
| WO | WO95/20155 A1 | 7/1995 |
| WO | WO98/10277 A1 | 3/1998 |
| WO | WO99/30145 A1 | 6/1999 |

* cited by examiner

*Primary Examiner*—Kaj K. Olsen
(74) *Attorney, Agent, or Firm*—Martin Fleit; Paul D. Bianco; Fleit Kain Gibbons Gutman Bongini & Bianco P.L.

(57) ABSTRACT

An apparatus for electrophoresis having a first gel matrix, adapted for performing an electrophoretic process therein, in communication with a second gel matrix, both being accommodated within a suitable housing. The housing has a first opening adapted to permit ionic communication between the first gel matrix and an external ionic buffer solution, and a second opening adapted to permit ionic communication between the second gel matrix and an external ionic buffer solution. The second gel has at least one suitable absorption material capable of retaining therein at least one target substance capable of migrating thereto from the first gel matrix when an electrophoretic process is performed in the first matrix.

17 Claims, 4 Drawing Sheets

GEL TRAP FOR ELECTROPHORESIS

RELATED APPLICATION

This application is a continuation of International Application No. PCT/IL01/01000 filed Oct. 29, 2001, the content of which is here incorporated in its entirety.

BACKGROUND OF INVENTION

1. Field of Invention

The present invention relates to a device or apparatus for gel electrophoresis, in particular, to such devices or apparatuses adapted for the safe handling and disposal of agarose-type gels containing dyeing compounds used therewith.

2. Prior Art

Gel electrophoresis, a commonly used method on molecular biology research, is a technique designed to separate, identify and purify DNA, RNA and protein molecules based on their weight, size and shape. This technique, which is simple and rapid to perform, is carried out by first preparing a gel. When the gel is ready it is placed in a gel box, immersed in a buffer solution, and connected to a power source. Once stimulated by the electric field that is set up in the gel, the molecules move through the gel matrix at different rates. The migration rate for each species of molecule is dependent upon the electrical charge, the size and shape of the molecules, as well as on the composition of the gel. Most commonly, the smaller molecules will move through the matrix at a quicker pace than those of a larger size. Sufficient quantity of buffer (typically TAE, TBE or protein running buffer) is generally used to ensure that the electric field is set up in the gel, and that the gel is covered with it and thus prevent the gel from drying out during electrophoresis. When loading a sample containing the molecule species of interest into the gel, a loading dye is typically used. The loading dye normally allows easy visualization of the solution during the loading process, as well as enabling the density of the sample to be increased to ensure that the sample is fully and evenly accommodated in a corresponding well in the gel, and further allows visualisation of the migration during electrophoresis.

The most commonly used gels are prepared with either agarose or acrylamide, either one of which can be provided in varying shapes, sizes and thicknesses. The deciding factor as to which particular gel and its physical attributes is generally related to the size of molecule being separated and the desired experiment to be performed by the user.

Acrylamide is usually chosen for relatively small molecules such as proteins, while agarose is used for larger molecules such as DNA or RNA, and agarose is the preferred choice for horizontal gel electrophoresis, typically cast in open trays by users.

Typically, it is desirable to visualize and to document the results of the electrophoresis separation test. In electrophoresis separation of DNA or RNA molecules, this may be accomplished by immersing the gel slab after the electrophoretic separation has been completed in a solution of a fluorescent compound which emits visible light when exposed to a ultraviolet (UV) light. Other methods of staining the gel are also known, for example by adding a suitable dye to the gel while casting the same. A widely used fluorescent compound is ethidium bromide. However, many types of such fluorescent compounds, including ethidium bromide, Acrydine Orange, SYBR Green I, and SYBR Green II, as well as acrylamide and also some components used together with some agarose gels, are toxic and/or carcinogenic, and contact with users must be strictly avoided, particularly when disposing of the gels after use.

It is therefore an aim of the present invention to provide a device and method which overcomes the limitations of prior art electrophoresis devices and methods.

It is another aim of the present invention to provide a device for enabling safe handling and disposal of gels which may contain harmful substances.

It is another aim of the present invention to provide such a device that is simple to use.

It is another aim of the present invention to provide such a device that is relatively simple mechanically and thus economic to produce.

It is another aim of the present invention to provide such a device that is adapted for use with regular horizontal electrophoresis equipment.

These and other aims are accomplished in the present invention by providing a precast cassette for horizontal electrophoresis, in particular a disposable and closed cassette for horizontal electrophoresis. In particular, the cassette comprises preferably a pair of traps, one at each longitudinal end of the cassette, each trap comprising an absorption material for preventing toxic material from migrating out of the cassette. This is an important safety feature, particularly in view of the handling of the horizontal electrophoresis apparatus and of the cassette during use thereof, and more so in view of the disposability of the cassette, which thus minimizes the risk of human contact with toxic substances comprised in the cassette.

In the preferred embodiment, the cassette comprises a box-like construction, having a bottom flat base and four vertical walls joined thereto about its periphery, and an upper cover mountable onto the vertical walls to define a gel chamber into which gel may be precast. The cassette also comprises openings at two opposite ends of the bottom base to enable ionic communication between the gel and an electrolytic solution in which the cassette may be partially immersed. The openings are preferably comprised in downwardly extending hollow leg members running the transverse length of the cassette at two longitudinal ends thereof, the leg members comprising gel in ionic communication with the main body of gel within the cassette. This design is particularly adapted for using the cassette with standard ion exchange chambers. Activated carbon or the like is provided in the legs and also in a second trapping chamber to absorb dangerous materials such as the dyeing compounds.

U.S. Pat. No. 3,888,759 discloses a gel cassette having a substantially box-like construction, having a downwardly depending transversely extending hollow leg at each longitudinal end of the cassette. The device appears to be reusable, providing the user with different options, and it appears intended for the user to cast the gel each time, rather than providing a precast package. There is no disclosure or suggestion of a trap for toxic materials, and in fact teaches away from this concept.

U.S. Pat. No. 5,443,704 discloses a substantially box-like container assembly for packaging prefabricated gels, containing more than one precast gel in a stacked arrangement. No trap for harmful substances is disclosed therein.

U.S. Pat. No. 5,064,769 discloses a gel for immunoassay of a single protein species in which the horizontal gel comprises a first part made from acrylamide gel having a proportion of agarose (0.7%) and a second part made from agarose gel. No trap for harmful substances is disclosed therein.

In U.S. Pat. No. 3,930,983 an arrangement and process are disclosed for determining antigens, in which a support plate is coated with an agar or agarose as a matrix in successive gel strips. No trap for harmful substances is disclosed therein.

U.S. Pat. No. 5,582,702 is directed to a self-contained electrophoresis apparatus comprising a housing having a gel body accommodated therein together with ion exchange matrices and electrodes, which are electrically connectable to an external power source. The apparatus is thus not generally compatible with existing ion exchange chambers currently used for horizontal electrophoresis. While it is presented as optionally "disposable", the apparatus is nonetheless complex, and does not appear inexpensive in comparison with simple precast gels, such as those described in U.S. Pat. No. 5,443,704, for example. Moreover, the apparatus contains elements which are not normally considered disposable, notably the electrodes and ion exchange matrices. In fact by being fully closed, in particular regarding the lower side thereof, the apparatus cannot be used with standard ion exchange apparatuses, and thus needs a dedicated stand having electrical connection points for the electrodes. Optionally, ethidium cations may be released into the gel by one of the ion exchange matrices within the housing, which may be simply disposed after use. However, and as stated earlier, the complexity of the apparatus renders this a rather expensive solution for the disposal of the contaminated gel. Furthermore, no traps are actually provided for retaining the contaminants therein—therefore, if any openings were to be made, for example, at the lower part of the cassette, for example as in the present invention, the contaminants could flow out, in contrast thereto.

EP No. 471949 discloses a capillary tube for performing capillary zone electrophoresis. The tube is modified by including a polystyrene frit that divides the tube into a downstream free zone, and an upstream zone which can comprise a polyacrylamide stacking gel. The gel plug functions as a filter to pre-treat the samples that are to be analyzed in the free zone of the tube. This is in contrast to the present invention, wherein the traps are placed downstream to treat the contaminants in the gel during and at the end of the electrophoretic process, and not prior to the beginning thereof. In fact, the samples in the present invention do not generally require pretreatment as described in this patent. Furthermore, the present invention uses agarose gel with an absorption material for retaining therein a target substance. On the other hand, in EP No. 471949 uses polyacrylamide, which is also toxic and use thereof would be detrimental in the present invention as a trapping gel, and in fact, counterproductive for this purpose. Thus, this publication teaches away from the present invention.

WO92/17259 describes a method for identifying a solute of interest in an effluent stream. A sample containing the mixture to be separated is passed through a first system capable of partitioning the components of the mixture, and a detector provides a first output that describes the temporal and/or spatial sequence of components exiting the first system. The effluent stream is then passed through a second system capable of extracting a solute of interest from the effluent, and a detector provides a second output that describes the temporal and/or spatial sequence of components exiting the second system, which no longer includes the solute of interest. The solute of interest can then be identified in the first output by comparing this to the second output. This method is thus directed at identifying a substance in a first separating system by employing a parallel second separating system, and is thus very different to the present invention, in which only a single electrophoresis process is employed, the target substance being removed during that process. WO 92/17259 does not address the problem of, nor does it provide a solution for, the trapping of toxic substances in an electrophoresis process, less so in the manner of the present invention.

WO 95/20155 relates to a sample holder in the form of a well, into which a sample and a first molten gel is introduced. When the first gel/sample mixture has solidified, the sample holder is applied against one end of a second gel slab, such as to bring the first gel/sample solidified mixture in ionic contact with the second gel. At no time is the first gel in solidified form brought into contact with the second gel prior to introducing the sample. WO 99/30145 relates to a slotted electrophoresis gel composition and methods for use, for providing a multilayered gel for vertical gel electrophoresis. It does not address, nor provide a solution for, the problem of forming stable sample wells for horizontal electrophoresis in an acrylamide gel. These publications do not address the problem of, nor do they provide a solution for, the trapping of toxic substances in an electrophoresis process, less so in the manner of the present invention Other publications of background relevance to the present invention include WO 98/10277, U.S. Pat. No. 5,228,971, U.S. Pat. No. 5,827,418, U.S. Pat. No. 3,873,433, EP No. 971229, WO 95/14921, DE 3232685, EP No.199470 and U.S. Pat. No. 3,803,020.

SUMMARY OF INVENTION

The present invention relates to an apparatus for electrophoresis comprising a first gel matrix in communication with a second gel matrix, said first gel matrix and said second gel matrix accommodated within a suitable housing, said housing comprising at least one first opening and at least one said second opening, said at least one first opening being adapted to permit ionic communication between said first gel matrix and an external ionic buffer solution, and said at least one second opening being adapted to permit ionic communication between said second gel matrix and an external ionic buffer solution, wherein said first gel matrix adapted for performing an electrophoretic process therein, and wherein said second gel comprises at least one suitable absorption material capable of retaining therein at least one target substance capable of migrating thereto at least from the said first gel matrix when an electrophoretic process is performed in said first matrix.

Typically, electrophoresis of a sample is conducted in said first gel matrix in a direction substantially away from said second gel matrix, and the said first gel matrix may comprise suitable wells adapted for introducing therein samples of interest to be electrophoresed. The first gel matrix is accommodated in a first chamber within said housing and said second gel matrix is accommodated in a second chamber within said housing, said first chamber being in communication with said second chamber.

Optionally, the apparatus further comprises a third gel matrix accommodated in said housing and in communication at least with said first gel matrix, wherein ionic communication between said first gel matrix and an external ionic buffer solution is via said third gel matrix and via said at least one first opening, and wherein said third gel matrix comprises a suitable absorption material capable of retaining therein a target substance capable of migrating thereto at least from the said first gel matrix when an electrophoretic process is performed therein in a direction substantially towards said second gel matrix.

In the preferred embodiment, the housing further comprises a first substantially hollow leg member extending downwardly from said at least one first opening, said first leg member adapted for providing communication between said first gel matrix and an outside of said housing. Similarly, the housing further comprises a second substantially hollow leg member extending downwardly from said at least one second opening, said second leg member adapted for providing communication between said second gel matrix and an outside of said housing. The said first leg member typically comprises said third gel matrix, and a fourth gel matrix may be accommodated in said second leg member and in communication at least with said second gel matrix, wherein ionic communication between said second gel matrix and an external ionic buffer solution is via said fourth gel matrix and said at least one second opening, and wherein said fourth gel comprises a suitable absorption material capable of retaining therein a target substance capable of migrating thereto at least from the said first gel matrix when an electrophoretic process is performed therein in a direction substantially towards said second gel matrix.

The target substance is typically a suitable dyeing compound; the first gel matrix is made primarily from agarose; the second gel matrix is made primary from agarose mixed with said absorption compound; the third gel matrix is made primary from agarose mixed with said absorption compound; and the fourth gel matrix is made primary from agarose mixed with said absorption compound, typically activated carbon.

The present invention also relates to an apparatus for performing electrophoresis therein, comprising:

a housing comprising a first chamber adapted for accommodating therein a first gel for use in an electrophoretic process; and a second chamber adapted for trapping therein at least one target substance capable of migrating thereto at least from said first chamber, said first chamber being in communication with said second chamber;

said housing further comprising at least one first opening and at least one said second opening, said at least one first opening being adapted to permit ionic communication between a gel accommodated in said first chamber and an external ionic buffer solution, and said at least one second opening being adapted to permit ionic communication between a gel accommodated in said second chamber and an external ionic buffer solution.

In the preferred embodiment, the housing comprises at least a first base and peripherally joined walls defining said first chamber having a first longitudinal end and a second longitudinal end. The housing may also comprise at least a second base and peripherally joined walls defining said second chamber having a third longitudinal end and a fourth longitudinal end. The first chamber is partially superposed over said second chamber to define an area of horizontal overlap between said first chamber and said second chamber, and communication between said first chamber and said second chamber is via a suitable opening comprised in said area of horizontal overlap.

The housing is adapted for performing electrophoresis of a sample within said first chamber in a direction substantially away from said second chamber, and further comprises a suitable first gel matrix accommodated in said first chamber arranged such that migration occurs in a direction from said second end to said first end when said apparatus is used in an electrophoretic process. Typically, the first gel matrix comprises suitable wells adapted for introducing therein samples of interest to be electrophoresed.

The first gel matrix typically comprises a suitable dyeing compound, and the target substance may be such a dyeing compound, which may be harmful to humans.

The second chamber is adapted for trapping said target substance by accommodating therein a suitable second gel matrix, said second gel matrix characterized in comprising at least one suitable absorption material capable of retaining therein at least said target substance. A second gel matrix is accommodated in said second chamber within said housing, and a third gel matrix accommodated in said housing and in communication at least with said first gel matrix, wherein ionic communication between said first gel matrix and an external ionic buffer solution is via said third gel matrix and said at least one first opening, and wherein said third gel comprises a suitable absorption material capable of retaining therein a target substance capable of migrating thereto at least from the said first gel matrix when an electrophoretic process is performed therein in a direction substantially towards said second gel matrix.

In the preferred embodiment, the housing further comprises a first substantially hollow leg member extending downwardly from said at least one first opening, said first leg member adapted for providing communication between said first chamber and an outside of said housing. Similarly, the housing further comprises a second substantially hollow leg member extending downwardly from said at least one second opening, said second leg member adapted for providing communication between said second chamber and an outside of said housing. In this embodiment, the first leg member comprises said third gel matrix, and a fourth gel matrix is accommodated in said second leg member and in communication at least with said second gel matrix, wherein ionic communication between said second chamber and an outside of the housing is via said fourth gel matrix and said at least one second opening, and wherein said fourth gel comprises a suitable absorption material capable of retaining therein a target substance capable of migrating thereto at least from the said first gel matrix when an electrophoretic process is performed therein in a direction substantially towards said second gel matrix.

The target substance is typically a suitable dyeing compound; the first gel matrix is made primarily from agarose; the second gel matrix is made primary from agarose mixed with said absorption compound; the third gel matrix is made primary from agarose mixed with said absorption compound; the fourth gel matrix is made primary from agarose mixed with said absorption compound, typically comprising activated carbon.

The apparatus preferably further comprises a cover for releasably closing said first chamber. A suitable comb for forming wells in a gel may be accommodated in said first chamber, said cover comprising at least one suitable aperture for enabling said comb to penetrate into said first chamber.

Optionally, the cover comprises a tab in registry with and spaced from a platform comprised at said first longitudinal end of said device.

Advantageously, suitable adhesive strips are provided for reversibly sealing said bottom ends of said first and second leg members, respectively.

At least in the preferred embodiment, the housing is adapted to enable said apparatus to be used with standard electrophoresis devices having a pair of parallel juxtaposed buffer-containing toughs separated by an elevated platform for supporting said base of said housing, said first and second leg members extending sufficiently into corresponding said troughs to provide ionic communication at least between said third gel portion and buffer contained in one trough, and between said fourth gel portion and buffer contained in the other trough.

DETAILED DESCRIPTION OF PREFERRED EMBODIMENTS

The present invention is defined by the claims, the contents of which are to be read as included within the disclosure of the specification. The invention will now be described, by way of example, with reference to preferred embodiments taken in conjunction with the accompanying figures of the drawing.

The present invention relates to a device for horizontal electrophoresis which may be provided with any required macromolecule-separating compounds and any buffer compositions that are used for running macromolecules, as well as any required labelling compounds, characterized in comprising at least one suitable trap for trapping and retaining at least one of any such compounds therein, thereby minimizing contamination hazard to the external environment including users of the device.

Such an apparatus or device is preferably disposable, but may also be reusable for a host of applications. The term "disposable" in the present application means that the devices are designed (in corresponding embodiments) to be thrown away or otherwise disposed off after one use with only negligible economic loss. Such negligible economic loss may be comparable, for example, to the economic loss incurred in disposing of plastic pipettes for handling liquids or eppendorf tubes. While these items may be used more than once, they are nonetheless typically thrown away after a single use, this being more cost effective than cleaning and/or sterilizing the same for subsequent use.

Referring to the figures, FIGS. 1 to 4 illustrate a preferred embodiment of the present invention. The apparatus or cassette, designated by the numeral (1), comprises a housing (100) of a box-like construction, a suitable gel (38) for electrophoresis, accommodated in a first chamber (30), and a second suitable gel for trapping dangerous substances therein, accommodated in a second chamber (40).

Figure 1:
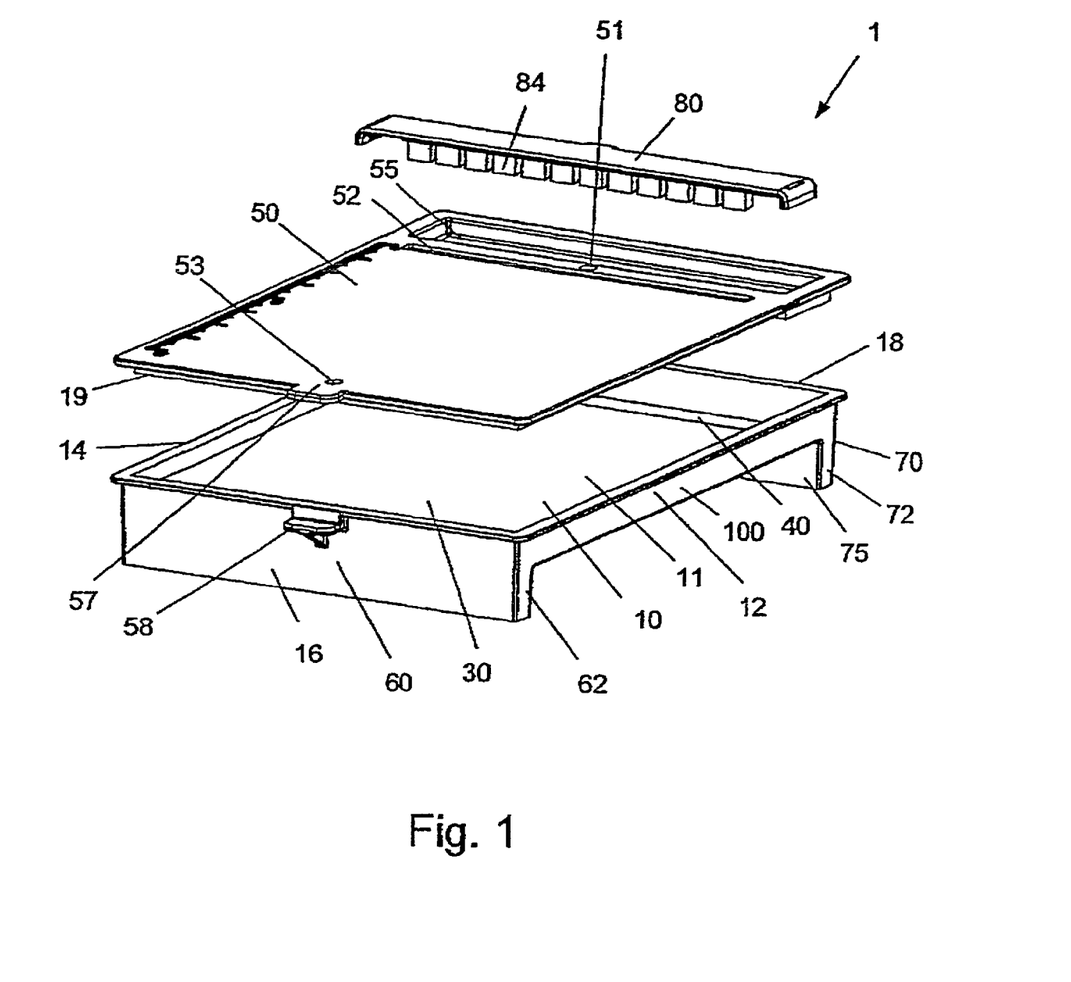
FIG. 1 shows in exploded perspective view the main elements of a preferred embodiment of the present invention.
Figure 2:
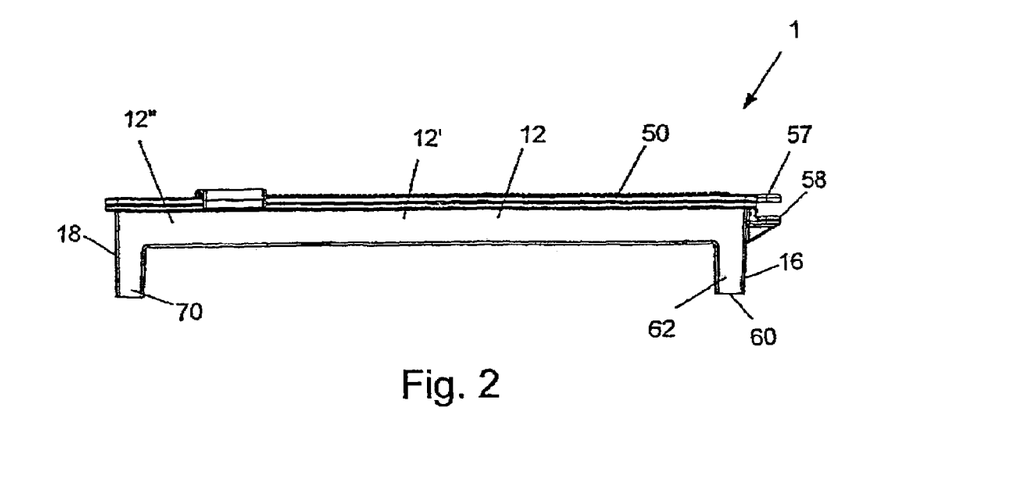
FIG. 2 shows in side view the embodiment of FIG. 1 assembled.
Figure 3:
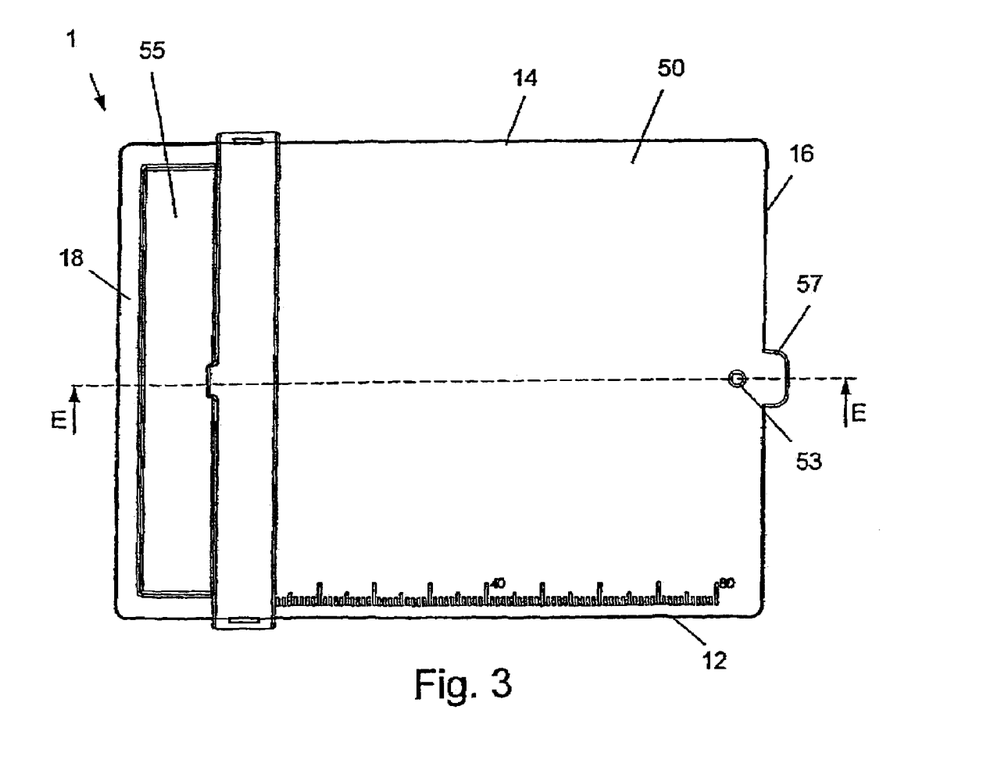
FIG. 3 shows in top view the embodiment of FIG. 2.
Figure 4:
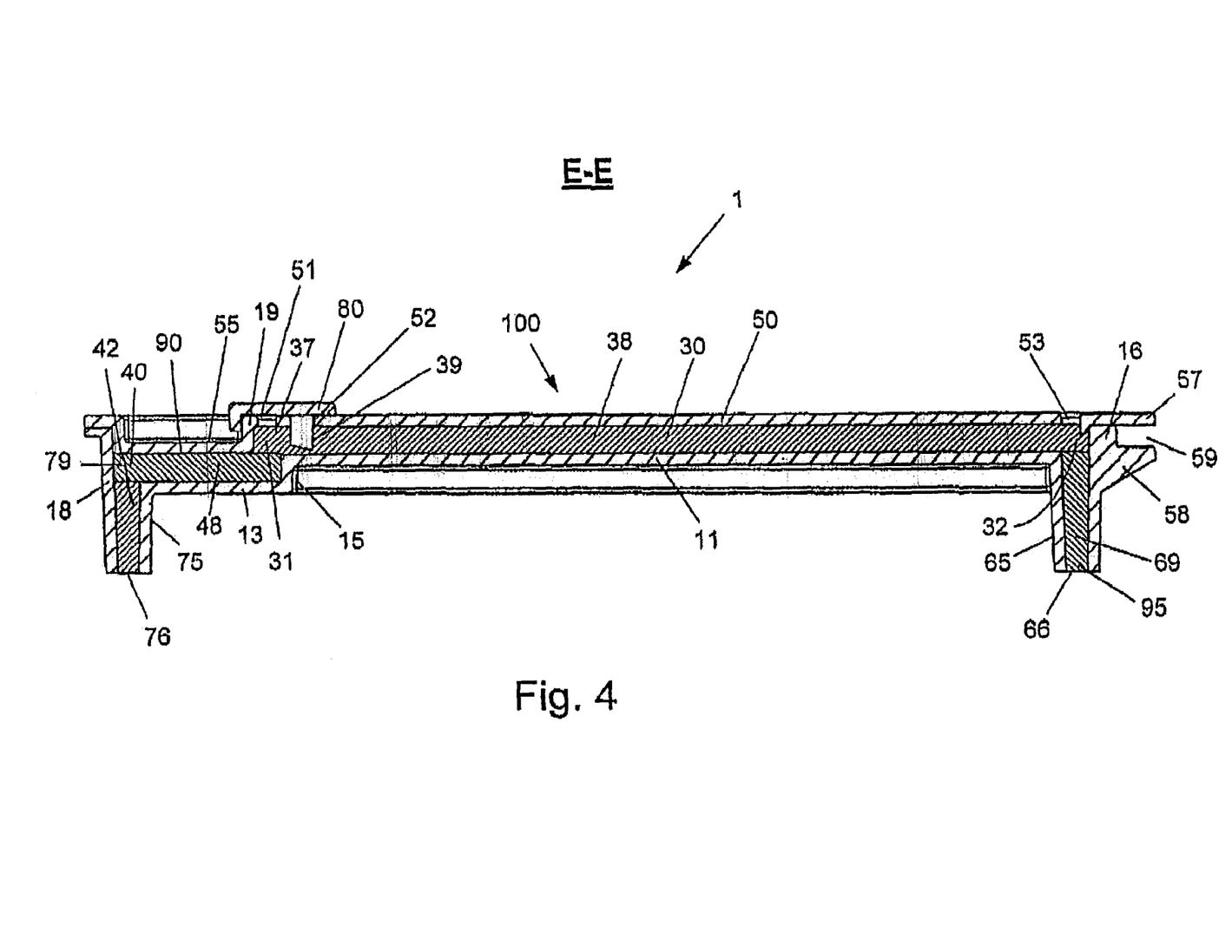
FIG. 4 shows in side elevational cross-sectional view, the embodiment of FIG. 3 taken along line E-E.

The cassette (1) comprises a stepped bottom base (10) having a flat upper part (11) and a flat but shorter lower part (13) joined longitudinally one to the other by a first intermediate vertical wall (15). Two side walls (12), (14) run the longitudinal length of the cassette (1) and are preferably integrally joined to the base (10) and to end walls (16) and (18) at opposite longitudinal ends of the cassette (1). A second intermediate wall (19) is joined to side walls (12) and (14) at a longitudinal location between first intermediate wall (15) at the end wall (18) closest thereto. The second intermediate wall (19) substantially divides each side wall (12) and (14) longitudinally into longer portions (12') and (14'), respectively, extending between the end wall (16) and intermediate wall (19), and shorter portions (12") and (14"), respectively, extending between the intermediate wall (19) and the other end wall (18). The upper edge of the second intermediate wall (19) is substantially coplanar with the upper edge of end wall (16) and with the upper edges of at least the longer side wall portions (12') and (14'), and thus enable an upper cover (50) to be releasably and sealingly mounted thereonto. Upper cover (50) may comprise optionally closable apertures (51) and (53) longitudinally spaced one from the other along the mid-line of the cover (50). These apertures (51), (53) facilitate pouring of gel into the cassette (1) when the cover (50) is in place, described in greater detail hereinbelow. Thus, the second intermediate wall (19), end wall (16) and the longer side wall portions (12') and (14'), together with upper cover (50) and the upper part (11) of the base (10) define the first chamber (30) of the cassette (1). The second chamber (40) of the cassette is correspondingly defined by the second intermediate wall (19), end wall (18) and the shorter side wall portions (12") and (14"), together with upper wall (55) and the lower part (13) of the base (10). Upper wall (55) may optionally be joined typically integrally with the second intermediate wall (19), end wall (18) and the shorter side wall portions (12") and (14"). Preferably, though, and as illustrated in FIGS. 1 and 4, upper wall (55) is integrally joined to the upper cover (50) and is releasably and sealingly mountable onto the upper edges of the second intermediate wall (19), end wall (18) and the shorter side wall portions (12") and (14"). The lower edge of the second intermediate wall (19), however, does not extend as far as the lower part (13) of the base (10), and thus communication between the first chamber (30) and second chamber (40) is provided by virtue of the longitudinal gap between the first and second intermediate walls, (15) and (19), respectively.

Thus, in the preferred embodiment, the first chamber (30) is partially superposed over the second chamber (40), defining an area (31) where the two chambers overlap horizontally. At least a portion of this area (31) has an opening, or preferably is open, providing communication between the first chamber (30) and the second chamber (40).

Preferably, the cassette (1) or other embodiments thereof is provided with a suitable first gel matrix (38) accommodated in the first chamber (30) and a suitable second gel portion (48) is accommodated in the second chamber (40). Alternatively, the cassette (1) or other embodiments thereof may be provided without one or both these gels, which can be cast as and when needed. In any case, the first gel matrix (38) is adapted for performing electrophoresis therein, and typically comprises at least one dyeing compound. The term dyeing compound is taken herein to include any type of labelling substance that may be used to identify the molecules of interest in the sample being electrophoresed in the first gel matrix (38). The second gel matrix (48) is adapted for trapping and retaining therein at least one target substance capable of migrating thereto at least from the first gel (38) during electrophoresis, and dyeing compounds are typically such target substances. The second gel matrix is typically adapted for trapping by comprising an absorbent material mixed therewith and which prevents the target substance from exiting the second gel (48).

Top cover (50), and preferably the rest of housing (100) is made from any suitable ultraviolet-transparent material. Preferably, the whole of the cassette (1), in particular the housing (100), is made from an economically disposable material.

Optionally, a tab (57) is provided at one end of the cover (50), and a corresponding platform (58) is provided at end (16), preferably integrally joined thereto, such that the tab (57) is in registry with platform (58) and mutually spaced by space (59) when the cover (50) is in place over chamber (30). By placing a suitable flattened tool such as a screwdriver or key (not shown), for example, within space (59) and rotating it by 90°, say, the cover (50) may be snapped open and thus removed from the chamber (30).

Having an openable cover (50) is important in applications, for example, where it is required to remove some of the first gel portion (38) for further processing such as electroelution or transfer of molecules from the first gel portion (38) to a membrane (western blot or northern blot).

The cassette (1) also comprises openings at two opposite ends of the bottom base (10) to enable ionic communication between the gel that is accommodated in the cassette (1) and an electrolytic solution in which the cassette (1) may be partially immersed. Thus, transverse opening (32) at longitudinal end of the upper part (11) of the base (10) near end wall (16) provides communication between the first chamber (30) and the outside of the cassette (1). Similarly, transverse opening (42) at longitudinal end of the lower part (11) of the base (10) near end wall (18) provides communication between the second chamber (40) and the outside of the cassette (1).

Openings (32) and (42) serve to provide ionic communication between the gels accommodated within the cassette (1) and external ionic solutions, and thus enable electrophoresis to be conducted within the cassette (1) with the provision of a suitable electric field. Preferably, though, the openings at the bottom base (10) are in the form of substantially hollow leg members running the transverse length of the cassette (1) at two longitudinal ends thereof, the leg members also being capable of accommodating gel in ionic communication with the main body of gel accommodated within the cassette (1). This inverted-U design is particularly adapted for using the cassette (1) with standard ion exchange chambers, which are generally in the form of two juxtaposed buffer-containing troughs separated by an elevated platform which is ideal for supporting the base (10) of cassette (1). One leg member is extends into one trough, and the other leg member into the second trough to provide ionic communication at least between the gel contained in the legs and the corresponding buffer solutions in the troughs. One trough has a cathode and the other trough has an anode.

Thus, the cassette (1) optionally, and preferably, comprises hollow legs (60) and (70) provided at opposite longitudinal ends thereof. At one end of the cassette (1), leg (60) is defined by a downwards extension of end wall (16), together with downwardly extending tab-like projections (62) at the end of longer side wall portions (12") and (14"), respectively, and a fourth wall (65) projecting downwards from the upper part (11) of base (10). Similarly, leg (70) at the other longitudinal end of the cassette (1) is defined by a downwards extension of end wall (18), together with downwardly extending tab-like projections (72) at the end of shorter side wall portions (12') and (14'), respectively, and a corresponding fourth wall (75) projecting downwards from the lower part (13) of base (10). Each leg (60), (70) are open at the corresponding bottom ends (66), (76) thereof, which may be temporarily closed (at least prior to use of the cassette (1)) by means of suitable removable adhesive strips (not shown) adhered thereto. The bottom ends (66), (76) are in communication with the first chamber (30) and second chamber (40), respectively, via the transverse openings (32) and (42), respectively.

The first chamber (30) is thus adapted to accommodate a suitable gel matrix (38) adapted for electrophoresis, preferably comprising a plurality of wells (39) for accepting samples that are to undergo an electrophoretic process. The gel matrix (38) typically comprises an agarose gel, though alternatively it may comprise other types of gels, included multilayered gels, which comprise strips of different gels or gel compositions juxtaposed one with another sequentially. Alternatively, the gel matrix (38) may comprise a hybrid gel matrix having a substantially solidified first gel portion juxtaposed with at least a substantially solidified second gel portion, wherein the first gel portion is capable of accommodating therein at least one sample for electrophoresis after said first gel portion is in solidified form, and is generally made from or contains sufficient agarsose to provide a stable well structure for accommodating samples, and the second gel portion is adapted for enabling an electrophoresis process to be applied to such a sample that may be accommodated in said first gel portion, the second gel portion comprising an acrylamide gel. Such hybrid gels are disclosed in co-pending Israel Patent Application No. 139446, filed by Applicants.

The wells (39) may be formed by a comb (80), for example, having teeth (84) that are typically inserted into the first gel portion (37) via corresponding apertures (52) comprised in the cover (50). Alternatively, a common slit may be provided in the cover (50) in place of the individual apertures (52). Typically, the comb (80) is kept in place engaged with respect to the cover (50) until the cassette (1) is used, whereupon samples may be introduced into one or more wells (39) via corresponding apertures (52). After use, and before disposing of the cassette (1), the apertures (52) are preferably again closed by means of the comb (80).

The agarose gel (38) is preferably provided precast in the first chamber (30), though may be alternatively cast by users in some applications. In any case, the gel may be poured into the first chamber (30) having first removed the cover (50). Another method of casting the gel is by turning the cassette (1) vertically such that the end wall (16) is uppermost. Gel is then poured into the chamber (30) up to the required height (which corresponds to the end wall (16) when the cassette (1) is returned to its horizontal position). With this method, the gel may be poured into the chamber (30) via aperture (53). Other ways of casting the gel are also possible. Wells (39) may be formed in the normal manner using, for example, a comb (80). However, the step of casting the first gel matrix (38) is usually performed after the second gel matrix (48) is cast, as described hereinbelow.

According to the present invention, at least one trap, and preferably two traps are provided for preventing release of dangerous substances from the cassette (1) to the external environment. Many labelling compounds, as well as acrylamide gels, may be toxic and/or carcinogenic and therefore potentially harmful to the cassette operator and to the environment. Thus, a first trap (90) is provided in the form of the second chamber (40) for trapping and thus retaining labelling compounds and the like, and thus preventing the same from exiting the cassette (1). Second chamber (40) which is in open communication with first chamber (30), and at least in ionic communication therewith when both chambers are accommodating gels—is provided with a suitable second gel matrix (48), typically agarose gel having active carbon, silica gel (at a special pH condition), for example, or any other suitable absorption material, mixed therewith. The term absorption material is taken herein to include any type of material capable of retaining therein at least one target substance, such a target substance being typically capable of migrating in an electrophoretic process. Particularly when the cassette (1) is used with precast agarose gels, the dye compounds which are used originally for visualizing the molecules being separated, are provided mixed with the agarose gel in the first chamber (30), thereby removing the hazard associated with handling of these compounds prior to use of the cassette (1). Under electrophoresis, molecules of interest contained in samples provided at the wells (39) migrate from the wells (39) towards the end wall (16). At the same time, dyeing compounds such as ethidium bromide comprised in the gel migrate in the opposite direction, i.e., towards end wall (18), thereby arriving at the second chamber (40), and are prevented from leaving the second chamber (40) as well as leg (70) by virtue of the activated carbon particles or other suitable absorbent material comprised therein. Typically, electrostatic interactions build up between activated carbon particles and ethidium bromide leading to absorption of the latter within the appropriate gel matrix. A second trap (95) is provided at the other longitudinal end of the cassette (1) to absorb the dye compounds as the dye, when the user mistakenly runs the gel in an inverted configuration. In the latter situation, migration occurs from end (16) towards end (18), rather than the vice versa, and dye compounds are absorbed by the trap (95). The second trap (95) also prevents unwanted migration of dye compounds by diffusion forces when the cassette is not being used. This enables the cassette to have a relatively long shelf life, perhaps a year or more, for example. The second trap (95) is economically provided by the hollow leg (60), which comprises an third gel matrix (69) comprising an agarose gel having a quantity of activated carbon, silica gel (at a special pH condition), for example, and/or any other suitable absorption material mixed therein. Thus, even if openings (76) and (66) in legs (70) and (60), respectively, remain unsealed, the dyeing compounds will not run out due to their adherence to the absorption materials.

The traps (90), (95) are generally prepared before casting the gel in the first, electrophoresis, chamber (30). With the cover (50), including portion (55) off, and with the bottom ends of the legs (60) and (70) sealed with suitable adhesive peel-off tape, agarose gel (79), containing mixed therein a suitable proportion of activated carbon is poured into leg (70) and chamber (40), up to the level of the upper part (11) of base (10). Then, agarose gel (69), also containing mixed therein a suitable proportion of activated carbon or other suitable absorption material is poured into leg (60) and preferably also the second chamber (40), i.e. up to the level of the upper part (11) of base (10). When the gels (79) and (69) are set, the first gel matrix (38) may be poured and set in the first chamber (30) as hereinbefore described.

While trap (90) has been described as being in the form of a second chamber (40) at a level below the first chamber (30), this need not generally be so. Minimally, the trap (90) needs only to be adapted to provide ionic communication between the absorbent material comprised therein and the gel comprised in the first chamber (30), and situated with respect to the first chamber such as to be substantially downstream of the migration path of the dye compounds. Any configuration of trap (90) meeting these criteria are generally suitable. Thus, in a more simplified cassette, for example, a single chamber is provided, in which one end is provided with agarose gel containing absorption material, and this is juxtaposed with and in communication with a second body of gel within the chamber for electrophoresis.

While the cassette (1) preferably comprises both the traps (90), (95), the second trap (95) is generally not required.

Thus, optionally, a simpler cassette (1) may be provided without the he second trap (95), if it is so desired Further optionally, the cassette (1) may be provided without the said hollow legs (60) and (70), leading to a simplified structure. Thus communication between said first chamber (30) and external ionic solutions is via opening (32) in the base (10), and communication between said second chamber (40) and external ionic solutions is via opening (42) in the base (10).

Figure 5:
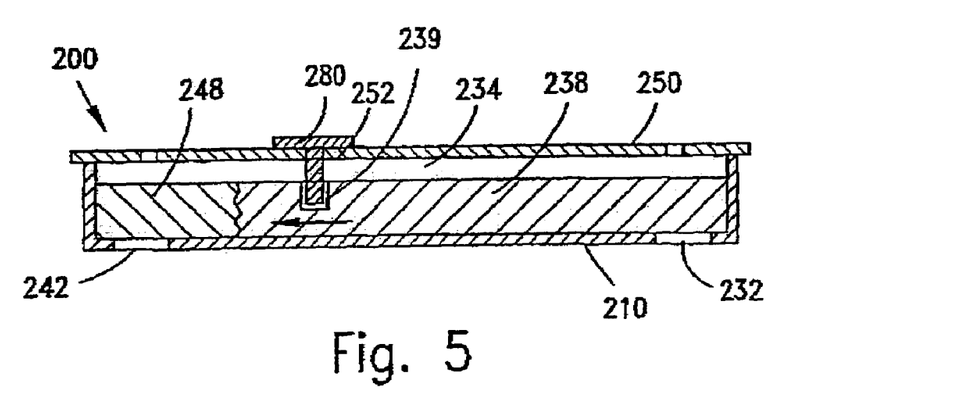
FIG. 5 shows in side elevational cross-sectional view, a second embodiment of the present invention.

Thus, referring to FIG. 5, a second embodiment of the present invention comprises a housing (200) having a base (210) and peripheral walls joined thereto at a lower end thereof, to define a chamber (234). A first gel matrix (238), similar to the first gel matrix (38) of the first embodiment, mutatis mutandis, and a second gel matrix (248) similar to the second gel matrix (48) of the first embodiment, mutatis mutandis, juxtaposed and in ionic contact with one another, are accommodated in the chamber (234). Thus, the first gel matrix (238) is adapted for performing electrophoresis, and may thus comprise dyeing substances and the like, while the second gel matrix (248) is adapted for trapping therein dangerous target substances such as these dyeing compounds, for example. The chamber (234) comprises openings (232) and (242) at longitudinal ends of the base (210) for providing ionic communication between the first gel matrix (238) and an external buffer solution, and between the second gel matrix (248) and an external buffer solution. Wells (239) are provided in the first gel matrix (238) for introducing samples to be electrophoresed. Optionally, a cover plate (250) may be provided, having suitable openings (252) for a comb (280) to be inserted therein to form wells (239).

Figure 6:
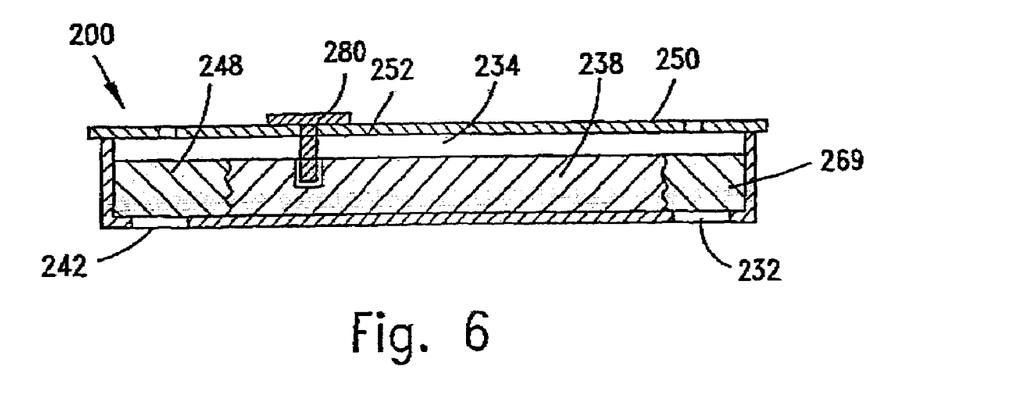
FIG. 6 shows in side elevational cross-sectional view, a third embodiment of the present invention.

A third embodiment of the present invention comprises all the components of the second embodiment as described above, mutatis mutandis, and is illustrated in FIG. 6. In addition, though, the chamber (234) further comprises a third gel matrix (269) juxtaposed and in ionic communication with the first gel matrix (238), but located at the opposed longitudinal end of the housing (200) with relation to the second gel matrix (248). The third gel matrix (269) serves as a precautionary second trap, and is thus similar to the third gel matrix (69) of the first embodiment, mutatis mutandis.

While in the foregoing description only a few specific embodiments of the invention are described in detail, it will be understood by those skilled in the art that the invention is not limited thereto, and that other variations in form and details may be possible without departing from the scope and spirit of the invention herein disclosed.

What is claimed is:

1. Apparatus for electrophoresis comprising a suitable housing accommodating a first gel matrix adapted for performing an electrophoretic process on at least one sample of interest therein in a first direction, characterized in comprising at least a first trap comprising a second gel matrix having at least one suitable absorption material capable of trapping and retaining therein at least one target substance migrating thereto from the first gel matux in an opposite direction to said first direction when an electrophoretic process is performed in said first matrix in said first direction, wherein said first gel matrix is in ionic conmiunication with said second gel matrix, and wherein said target substance is different from said at least one sample of interest.

2. Apparatus as claimed in claim 1, wherein said housing comprises at least one first opening and at least one said second opening, said at least one first opening being adapted to permit ionic communication between said first gel matrix and an external ionic buffer solution, and said at least one second opening being adapted to permit ionic communication between said second gel matrix and an external ionic buffer solution.

3. Apparatus as claimed in claim 2, wherein said first gel matrix comprises suitable wells adapted for introducing therein said samples of interest to be electrophoresed.

4. Apparatus as claimed in claim 2, wherein said first gel matrix is accommodated in a first chamber within said housing and said second gel matrix is accommodated in a second chamber within said housing, said first chamber being in communication with said second chamber.

5. Apparatus as claimed in claim 2, further comprising a second trap comprising a third gel matrix having at least one suitable absorption material capable of trapping and retaining therein at least one harmful target substance migrating thereto from the first gel matrix in said first direction when an electrophoretic process is performed in said first matrix in said first direction, wherein said first gel matrix is in ionic communication with said third gel matrix.

6. Apparatus as claimed in claim 5, wherein said third gel matrix is made primarily from agarose mixed with said absorption compound.

7. Apparatus as claimed in claim 2, wherein said housing further comprises a first substantially hollow leg member extending downwardly from said at least one first opening, said first leg member adapted for providing communication between said first gel matrix and an outside of said housing.

8. Apparatus as claimed in claim 7, wherein said first leg member comprises a third gel matrix.

9. Apparatus as claimed in claim 2, wherein said housing further comprises a second substantially hollow leg member extending downwardly from said at least one second opening, said second leg member adapted for providing communication between said second gel matrix and an outside of said housing.

10. Apparatus as claimed in claim 9, further comprising a fourth gel matrix accommodated in said second leg member and in communication at least with said second gel matrix, wherein ionic communication between said second gel matrix and an external ionic buffer solution is via said fourth gel matrix and said at least one second opening, and wherein said fourth gel comprises a suitable absorption material capable of retaining therein a target substance capable of migrating thereto at least from the said first gel matrix when an electrophoretic process is performed therein in a direction substantially towards said second gel matrix.

11. Apparatus as claimed in claim 10, wherein said fourth gel matrix is made primarily from agarose mixed with said absorption compound.

12. Apparatus as claimed in claim 1, wherein said target substance is a suitable dyeing compound.

13. Apparatus as claimed in claim 1, wherein said first gel matrix is made primarily from agarose.

14. Apparatus as claimed in claim 1, wherein said second gel matrix is made primarily from agarose mixed with said absorption compound.

15. Apparatus as claimed in claim 1, wherein said at least one absorption material comprises activated carbon.

16. Apparatus for performing electrophoresis therein, comprising:
a housing comprising
a first chamber adapted for accommodating therein a first gel matrix for performing an electrophoretic process on at least one sample of interest in a first direction; and
a second chamber adapted for trapping therein at least one target substance capable of migrating thereto at least from said first chamber in a direction opposed to said first direction, said first chamber being in communication with said second chamber;
said housing further comprising at least one first opening and at least one said second opening, said at least one first opening being adapted to permit ionic communication between a gel that may be accommodated in said first chamber and an external ionic buffer solution, and said at least one second opening being adapted to permit ionic communication between a gel that may be accommodated in said second chamber and an external ionic buffer solution;
said housing further comprises a first substantially hollow leg member extending downwardly from said at least one first opening, said first leg member adapted for providing comnmnication between said first chamber and an outside of said housing, said first leg member comprises a third gel matrix;
said housing further comprises a second substantially hollow leg member extending downwardly from said at least one second opening, said second leg member adapted for providing communication between said second chamber and an outside of said housing;
a fourth gel matrix accommodated in said second leg member and in communication at least with said second gel matrix, wherein ionic communication between said second chamber and an outside of the housing is via said fourth gel matrix and said at least one second opening, and wherein said fourth gel comprises a suitable absorption material capable of retaining therein a target substance capable of migrating thereto at least from the said first gel matrix when an electrophoretic process is performed therein in a direction substantially towards a second gel matrix.

17. Apparatus for performing electrophoresis therein, comprising:
a housing comprising
a first chamber adapted for accommodating therein a first gel matrix for performing an electrophoretic process on at least one sample of interest in a first direction; and
a second chamber adapted for trapping therein at least one target substance capable of migrating thereto at least from said first chamber in a direction opposed to said first direction, said first chamber being in communication with said second chamber, said second chamber accommodating therein a suitable second gel matrix, said second gel matrix characterized in comprising at least activated carbon, said activated carbon being capable of retaining therein at least said target substance;
said housing further comprising at least one first opening and at least one said second opening, said at least one first opening being adapted to permit ionic communication between a gel that may be accommodated in said first chamber and an external ionic buffer solution, and said at least one second opening being adapted to permit ionic communication between a gel that may be accommodated in said second chamber and an external ionic buffer solution;
said second chamber is adapted for trapping said target substance by accommodating therein a suitable second gel matrix, said second gel matrix characterized in comprising at least one suitable absorption material capable of retaining therein at least said target substance.

* * * * *